(12) United States Patent
Kojima

(10) Patent No.: US 10,397,514 B2
(45) Date of Patent: Aug. 27, 2019

(54) PROJECTION APPARATUS, IMAGE PROCESSING APPARATUS, AND IMAGE PROCESSING METHOD

(71) Applicant: CANON KABUSHIKI KAISHA, Tokyo (JP)

(72) Inventor: Naoki Kojima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/507,310

(22) PCT Filed: Oct. 1, 2015

(86) PCT No.: PCT/JP2015/005007
§ 371 (c)(1),
(2) Date: Feb. 28, 2017

(87) PCT Pub. No.: WO2016/072044
PCT Pub. Date: May 12, 2016

(65) Prior Publication Data
US 2017/0289493 A1    Oct. 5, 2017

(30) Foreign Application Priority Data

Nov. 6, 2014  (JP) ................................. 2014-226408

(51) Int. Cl.
*H04N 5/74*    (2006.01)
*H04N 9/31*    (2006.01)
(Continued)

(52) U.S. Cl.
CPC ............... *H04N 5/74* (2013.01); *A61B 5/055* (2013.01); *A61B 6/03* (2013.01); *G01R 33/54* (2013.01); *G06T 15/60* (2013.01); *H04N 9/3185* (2013.01)

(58) Field of Classification Search
CPC .......... G03B 21/00; G03B 21/14; H04N 5/74; H04N 9/31; G06K 9/32; G09G 5/37; G09G 5/02
See application file for complete search history.

(56) References Cited

U.S. PATENT DOCUMENTS 8,228,396 B2   7/2012  Hagiwara
8,750,646 B2   6/2014  Yoshimura
(Continued)

FOREIGN PATENT DOCUMENTS

CN   103034029 A   4/2013
JP   2001-069434 A  3/2001
(Continued)

OTHER PUBLICATIONS

Mar. 26, 2018 European Search Report in European Patent Appln. No. 15857669.4.
(Continued)

*Primary Examiner* — Cara E Rakowski
*Assistant Examiner* — Danell L Owens
(74) *Attorney, Agent, or Firm* — Venable LLP

(57) ABSTRACT

When deforming a first image into a second image and generating a third image which contains the second image, coordinate values indicating a position of each of a plurality of grid points after deformation disposed in the second image are stored, and it is determined whether or not a pixel of interest in the third image locates in the second image, based on the stored coordinate values.

13 Claims, 8 Drawing Sheets

(51) Int. Cl.
- *A61B 5/055* (2006.01)
- *A61B 6/03* (2006.01)
- *G01R 33/54* (2006.01)
- *G06T 15/60* (2006.01)

(56) References Cited

U.S. PATENT DOCUMENTS

| | | |
|---|---|---|
| 8,766,998 B1 | 7/2014 | Morgan, III et al. |
| 2010/0097502 A1 | 4/2010 | Hagiwara |
| 2010/0245393 A1 | 9/2010 | Moriya et al. |
| 2013/0083058 A1 | 4/2013 | Yoshimura |
| 2015/0022726 A1 | 1/2015 | Kojima |
| 2015/0077584 A1* | 3/2015 | Kunieda .............. G03B 21/147 348/222.1 |

FOREIGN PATENT DOCUMENTS

| | | |
|---|---|---|
| JP | 2001-083949 A | 3/2001 |
| JP | 2014-022836 A | 2/2014 |
| WO | 2008/139577 A1 | 11/2008 |

OTHER PUBLICATIONS

Paul Bourke, "Mesh format for image warping," Feb. 2006, XP055457307, URL:http://paulbourke.net/dataformats/meshwarp/, pp. 1-3.

Dec. 22, 2015 International Search Report and Written Opinion in International Patent Application PCT/JP2015/005007.

May 20, 2019 Chinese Official Action in Chinese Patent Appln. No. 201580059791.8.

* cited by examiner

[Fig. 1]
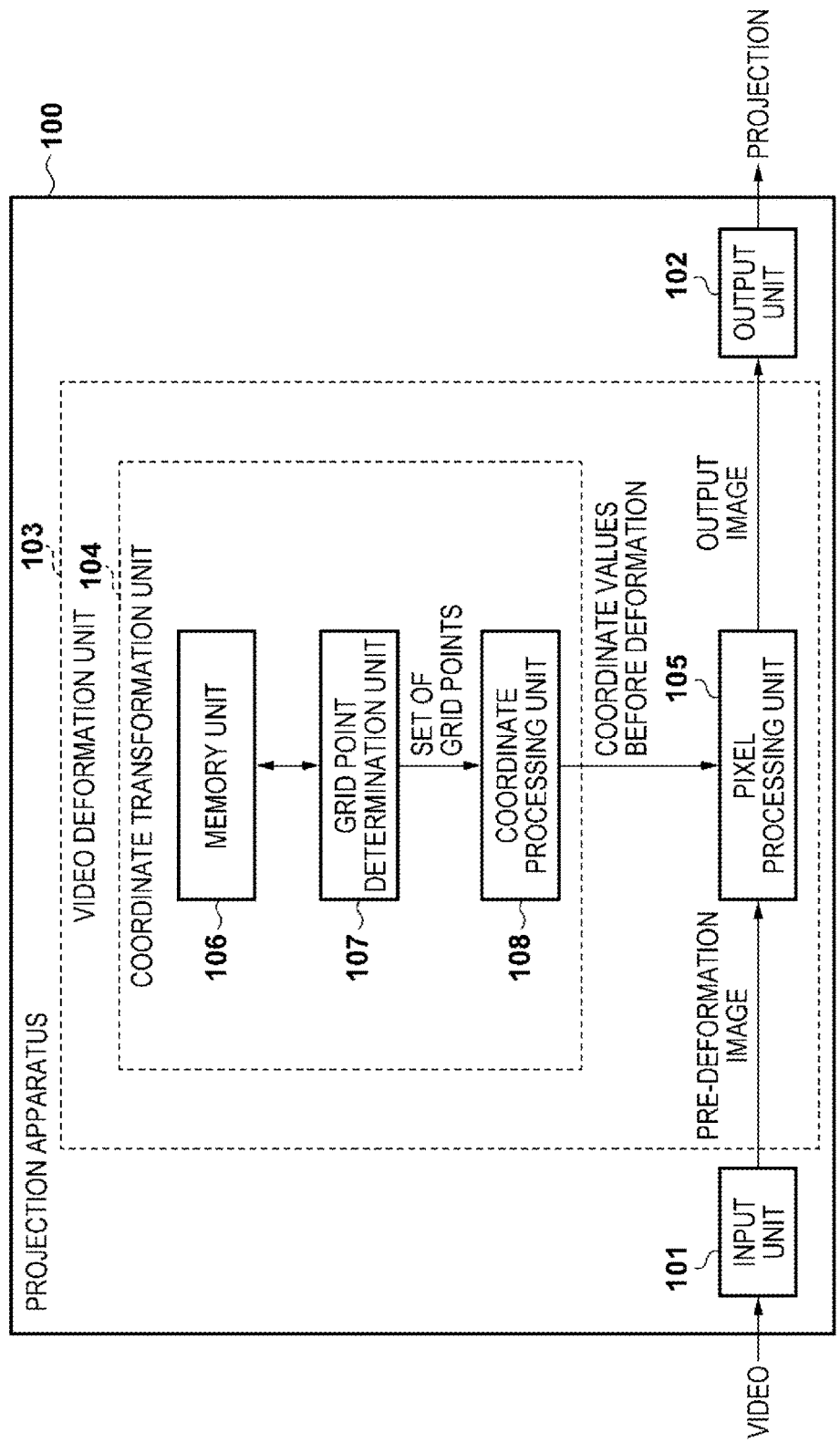

[Fig. 2A]
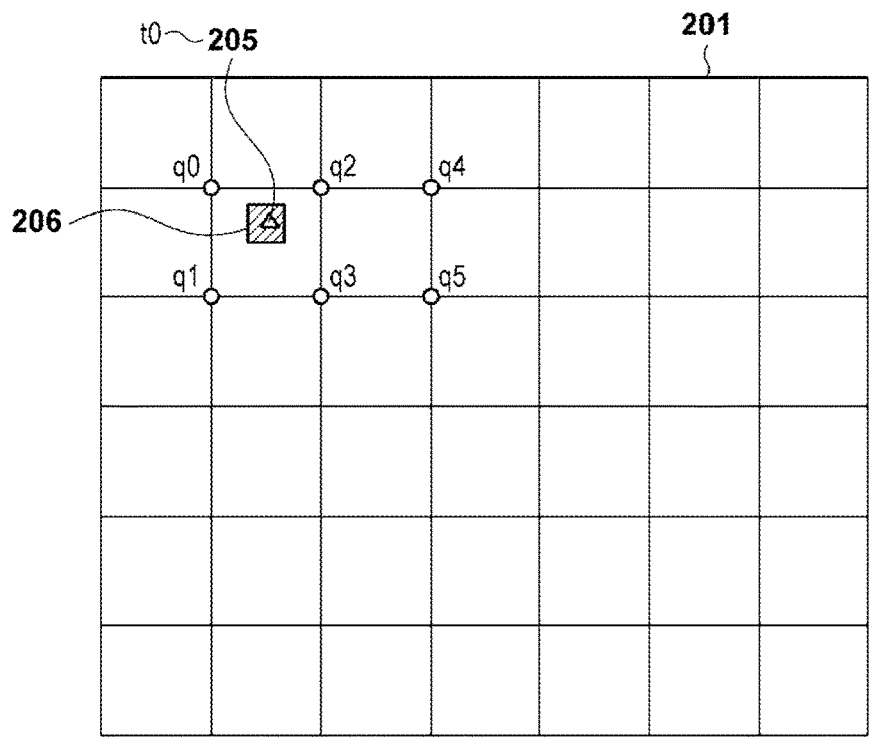
[Fig. 2B]
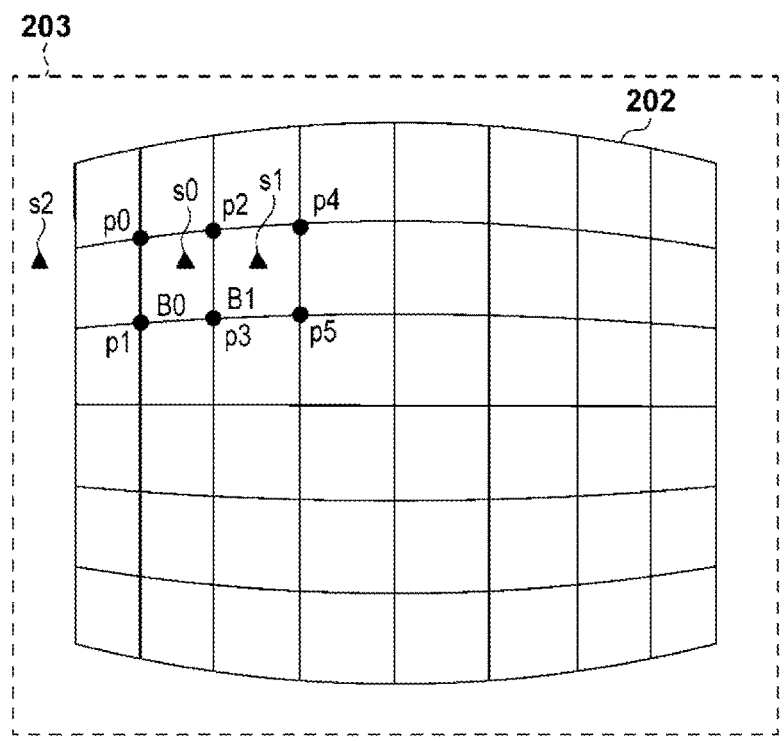

[Fig. 3]
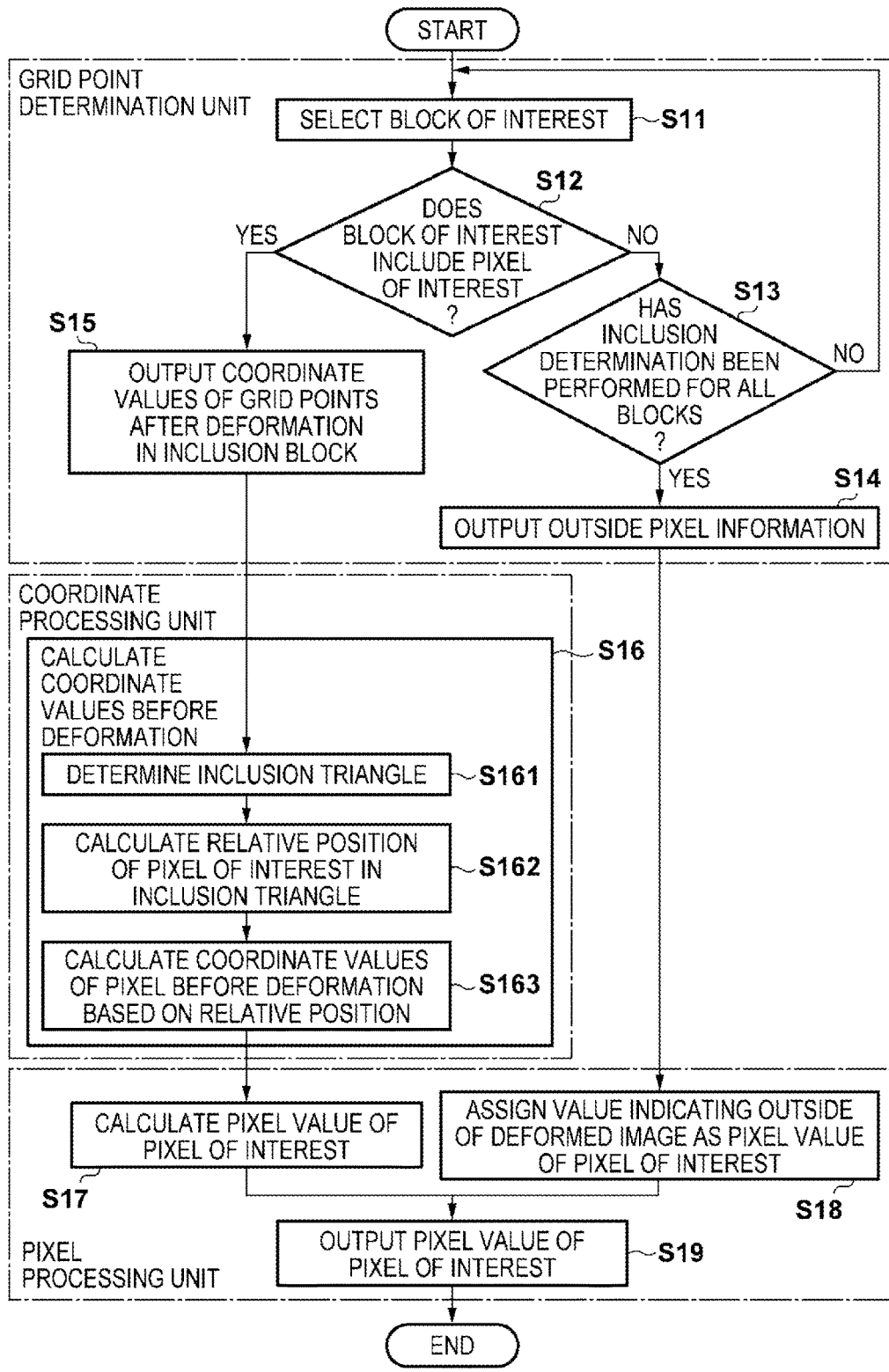

[Fig. 4A]
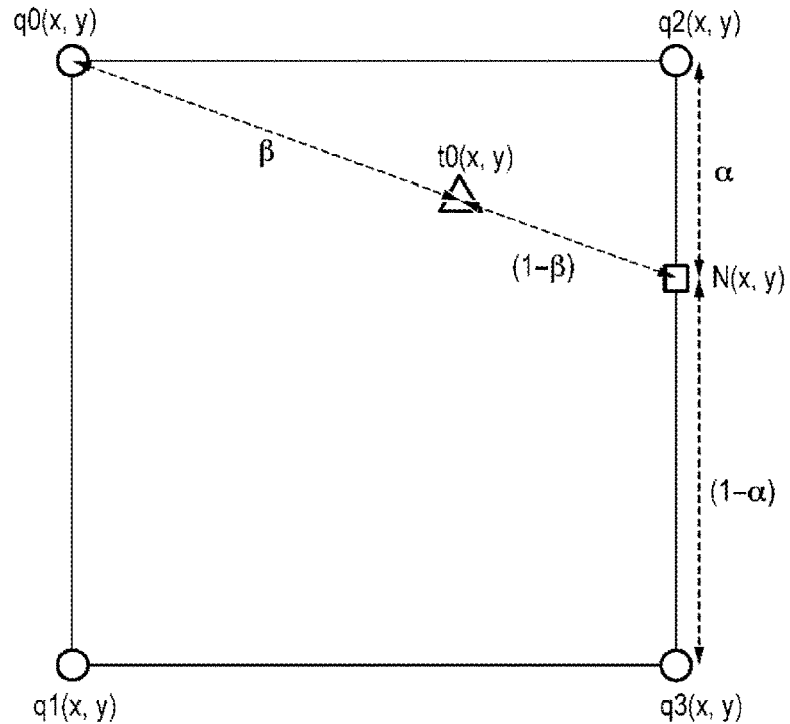
[Fig. 4B]
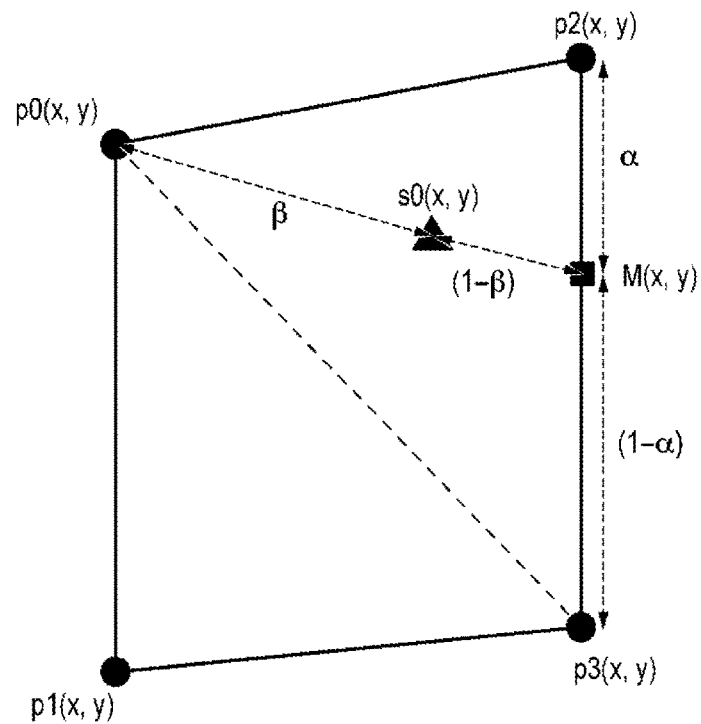

[Fig. 5]
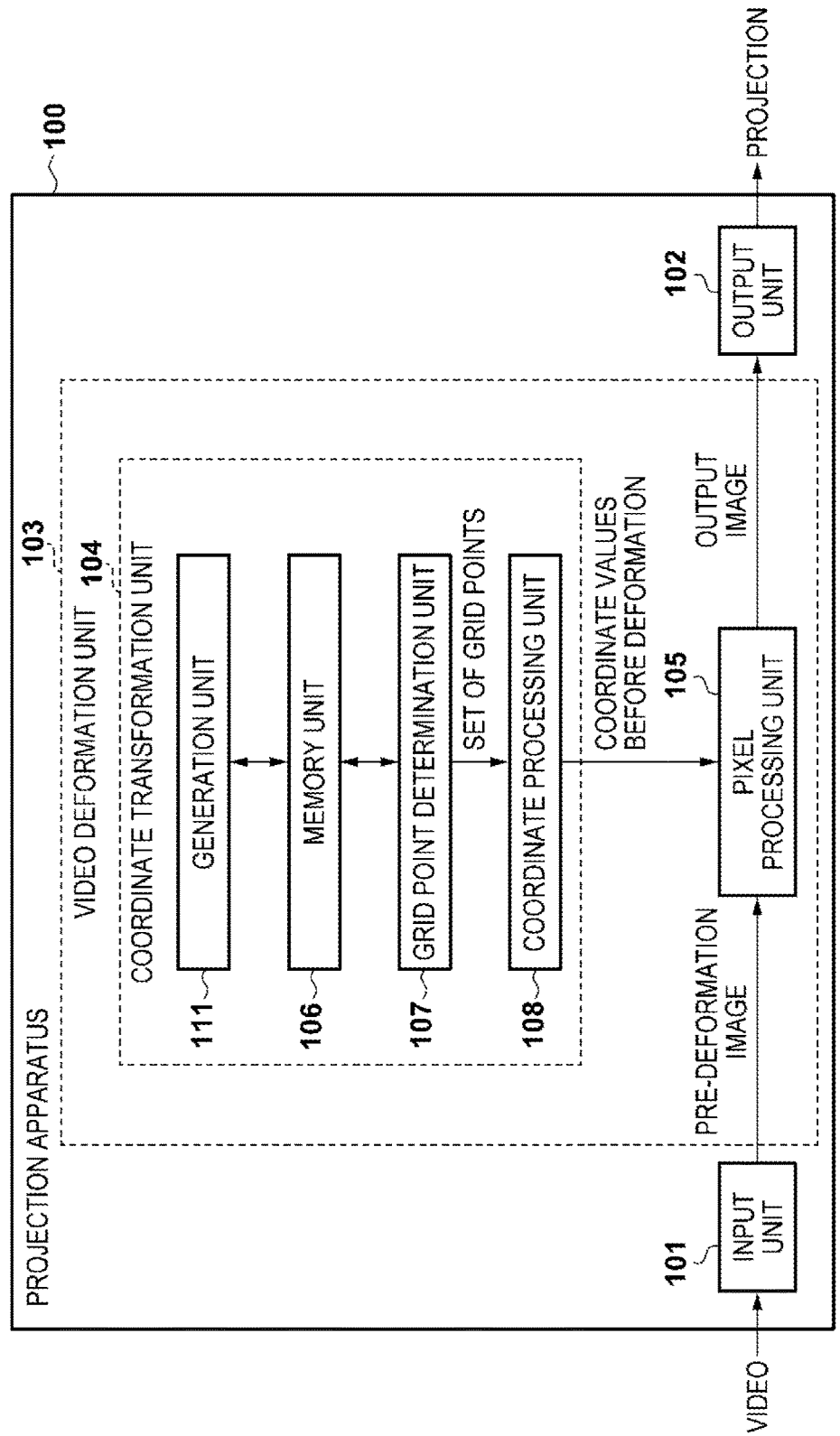

[Fig. 6]
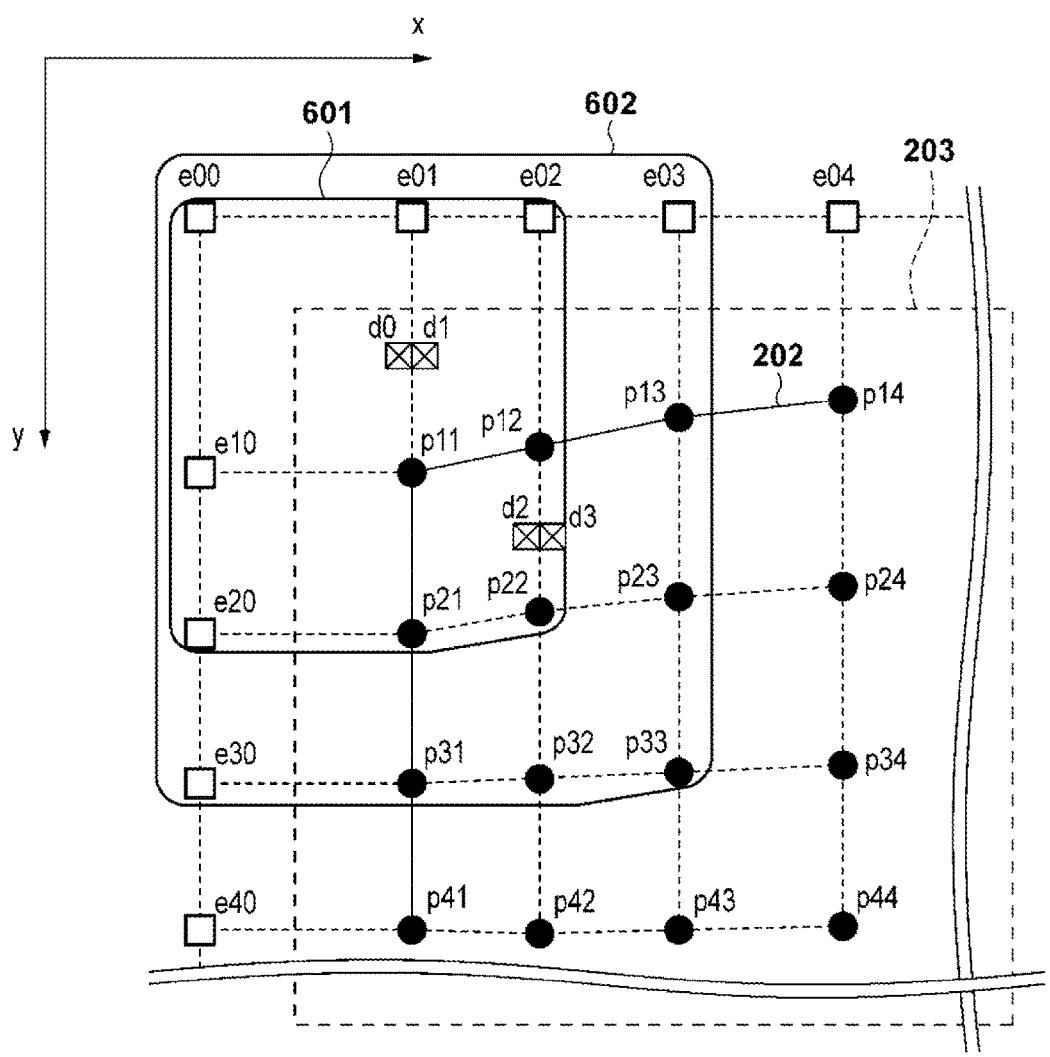

[Fig. 7]
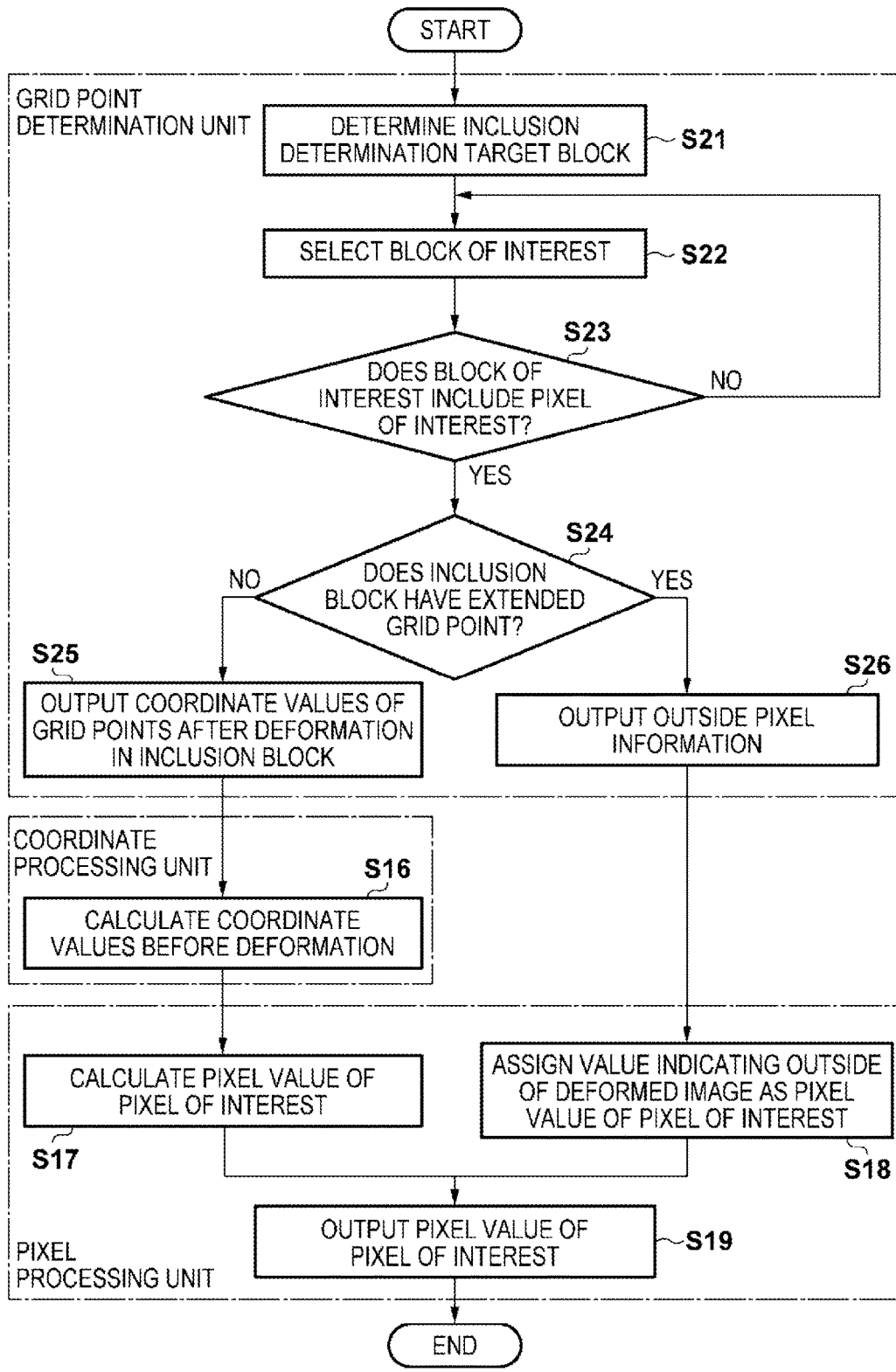

[Fig. 8]
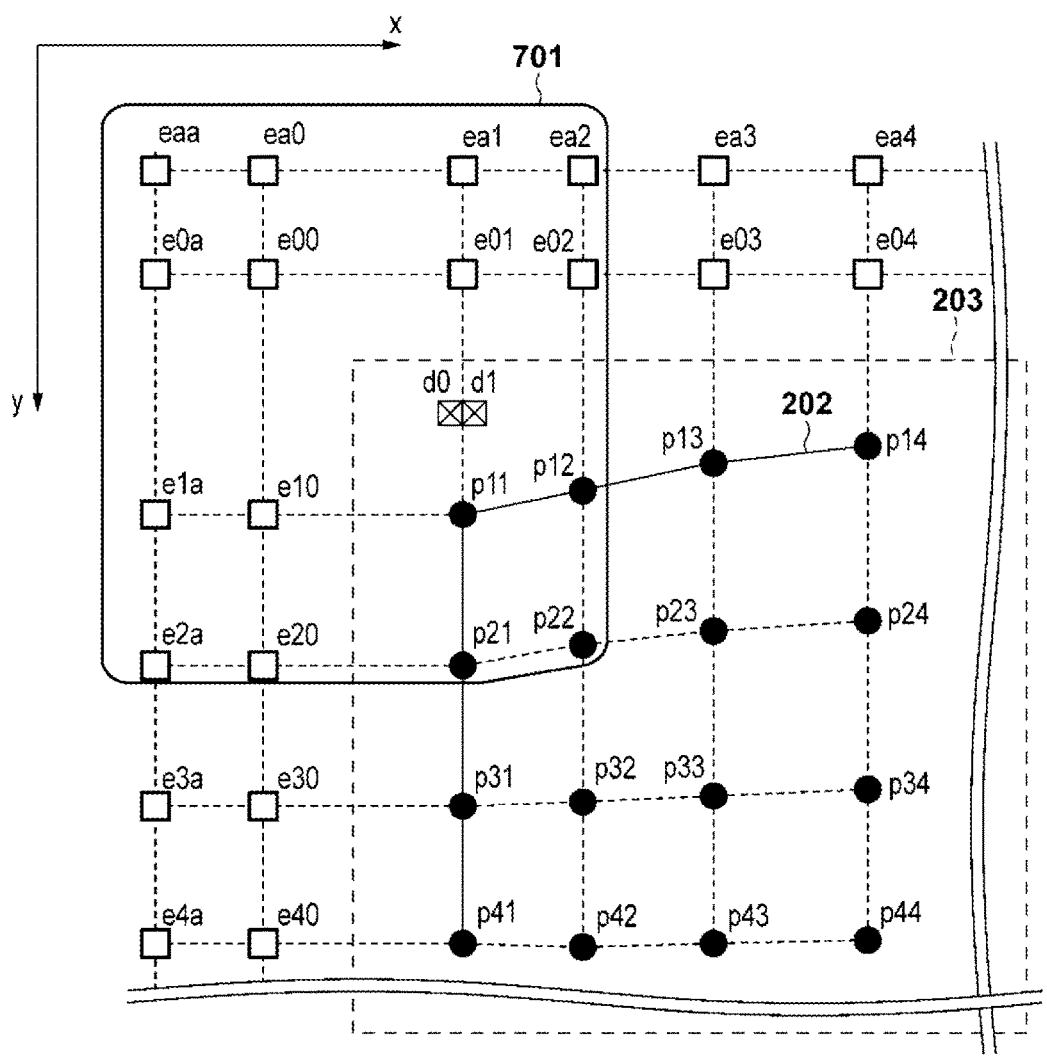

PROJECTION APPARATUS, IMAGE PROCESSING APPARATUS, AND IMAGE PROCESSING METHOD

TECHNICAL FIELD

The present invention relates to a projection apparatus, and an image processing apparatus and image processing method for generating a video to be supplied to the projection apparatus.

BACKGROUND ART

Recently, it is becoming popular to project videos not only to a flat surface but also to a curved surface such as a column or a dome. There is proposed a projection apparatus having an image deformation function so as to prevent a viewer from sensing the distortion of a video when projecting videos to various projection surfaces. The projection apparatus projects an image deformed in accordance with the projection surface, and the viewer can observe a video from which their does not feel a distortion.

However, if an image deformation arithmetic circuit for projecting an image from which a viewer does not feel a distortion is mounted in the projection apparatus for each of the shapes of various projection surfaces such as a cylindrical shape and a hemispherical shape, the circuit scale of the projection apparatus increases.

As a method for solving this problem, there is known a method of storing, in a memory, the coordinate values of grid points arranged in a pre-deformation image, and associating the respective grid points with locations in a deformed image. There is also known a method of storing, in a memory, the coordinate values of grid points disposed in a deformed image, and associating the respective grid points with locations in a pre-deformation image.

By using this association and the pixel value of a pixel of interest in a pre-deformation image, the pixel value of a pixel of interest in a deformed image can be obtained. This method can implement common use of the image deformation function regardless of the shape of the projection surface.

In general, calculation of a pixel value in the image deformation function for the projection apparatus is performed by inverse transformation rearrangement in order to prevent a missing pixel. More specifically, each pixel of a deformed image is set as a pixel of interest, and a coordinate values (to be referred to as a "coordinate values before deformation" hereinafter) before deformation that corresponds to the coordinate values of the pixel of interest are obtained by coordinate transformation. Then, the value of the pixel of interest is calculated using the value of a pixel (to be referred to as a "pixel of interest before deformation") corresponding to the coordinate values before deformation, and the values of pixels surrounding the pixel of interest before deformation.

As a method of obtaining a coordinate value before deformation, two methods are known: one is a method (to be referred to as a "post-deformation lattice method" hereinafter) using the coordinate values of grid points before deformation and the coordinate values of the grid points after deformation. The other is a method (to be referred to as a "pre-deformation lattice method" hereinafter) using the coordinate values of grid points after deformation and the inversely deformed coordinate values of the grid points before deformation.

International Publication No. 08/139577 (literature 1) discloses a pre-deformation lattice method in which transformed coordinate values (coordinate values before deformation) from those after deformation to those before deformation are stored in a memory as the coordinate values of grid points. According to the pre-deformation lattice method, in a deformation in which an image is reduced inward, grid points located outside the deformed image are located outside the deformed shape and become unnecessary. As a result, all grid points are not used for coordinate transformation, and the accuracy of coordinate transformation decreases. The decrease in the accuracy of coordinate transformation is a factor of image quality degradation such that, when deformed images are partially superposed to project the entire image at the time of, for example, combined projection by a plurality of projection apparatuses, displacement occurs between the deformed images, and as a result decreasing the sharpness of an image obtained by combining the deformed image.

Japanese Patent Laid-Open No. 2001-069434 (literature 2) discloses a post-deformation lattice method. The post-deformation lattice method requires a function of determining grid points to be used to calculate the coordinate values of a pixel of interest before deformation. In literature 2, coordinate values after deformation are used as the coordinate values of grid points, however any method of determining the grid points is not mentioned.

SUMMARY OF INVENTION

In one aspect, an image processing apparatus for deforming a first image into a second image and generating a third image which contains the second image, the apparatus comprising: a memory unit configured to store coordinate values indicating a position of each of a plurality of grid points after deformation disposed in the second image; and a determination unit configured to determine whether or not a pixel of interest in the third image locates in the second image, based on the coordinate values stored in the memory unit.

In another aspect, an image processing method of deforming a first image into a second image and generating a third image which contains the second image, the method comprising: storing coordinate values indicating a position of each of a plurality of grid points after deformation disposed in the second image; and determining whether or not a pixel of interest in the third image locates in the second image, based on the stored coordinate values.

According to these aspects, high-accuracy image deformation processing corresponding to an arbitrary deformation of a video becomes possible.

In an aspect, a video projection apparatus comprising the above image processing apparatus.

According to the aspect, a video from which a viewer does not feel a distortion of the video can be projected.

Further features of the present invention will become apparent from the following description of exemplary embodiments (with reference to the attached drawings).

BRIEF DESCRIPTION OF DRAWINGS

The accompanying drawings, which are incorporated in and constitute a part of the specification, illustrate embodiments of the invention and, together with the description, serve to explain the principles of the invention.

FIG. 1 is a block diagram showing the arrangement of a projection apparatus according to the first embodiment.

FIG. 2A is a view for explaining image deformation processing by a video deformation unit.

FIG. 2B is a view for explaining image deformation processing by the video deformation unit.

FIG. 3 is a flowchart for explaining image deformation processing to be executed by the video deformation unit according to the first embodiment.

FIG. 4A is a view for explaining calculation of a coordinate value before deformation by a coordinate processing unit.

FIG. 4B is a view for explaining calculation of a coordinate value before deformation by the coordinate processing unit.

FIG. 5 is a block diagram showing the arrangement of a projection apparatus according to the second embodiment.

FIG. 6 is a view showing a state in which extended grid points are added.

FIG. 7 is a flowchart for explaining image deformation processing to be executed by a video deformation unit according to the second embodiment.

FIG. 8 is a view showing another addition example of extended grid points.

DESCRIPTION OF EMBODIMENTS

A projection apparatus, an image processing apparatus, and an image processing method according to embodiments of the present invention will now be described in detail with reference to the accompanying drawings. Note that the embodiments are not intended to limit the present invention to the scope of the claims, and not all of the combinations of arrangements set forth in the embodiments are necessarily required with respect to the solution of the problems according to the present invention.

First Embodiment

Apparatus Arrangement

The arrangement of a projection apparatus 100 according to the first embodiment is shown in the block diagram of FIG. 1. The projection apparatus 100 comprises an input unit 101 that inputs a video, a video deformation unit 103 that performs image processing on the input video to deform the video, and an output unit 102 that projects the deformed video.

The video deformation unit 103 comprises a coordinate transformation unit 104 that calculates the coordinate values of a pixel of interest before deformation, and a pixel processing unit 105 that calculates the pixel value of the pixel of interest from the coordinate values of the pixel of interest before deformation and a pre-deformation image. The video deformation unit 103 executes image deformation processing as image processing in the projection apparatus 100.

The coordinate transformation unit 104 comprises a memory unit 106 that stores grid points after deformation, a grid point determination unit 107 that determines a set of grid points after deformation to be used for coordinate transformation of a pixel of interest, and a coordinate processing unit 108 that obtains the coordinate values of the pixel of interest before deformation using the determined set of grid points after deformation.

Image Deformation Processing

Image deformation processing by the video deformation unit 103 will be explained with reference to FIGS. 2A and 2B. The input unit 101 inputs a pre-deformation image 201 shown in FIG. 2A as the first image. The second image obtained by deforming the pre-deformation image 201 is a deformed image 202. More specifically, the video deformation unit 103 generates, from the pre-deformation image 201, an output image 203 shown in FIG. 2B as the third image including the deformed image 202, and outputs the output image 203 to the output unit 102. To generate the output image 203, the video deformation unit 103 calculates the pixel values of the respective pixels of the output image 203.

Next, the definition of grid points will be explained. A grid point corresponds to a representative point arranged in the pre-deformation image 201 or disposed in the deformed image 202, and is indicated by a coordinate value (x, y). The grid point corresponding to a representative point of the pre-deformation image 201 will be called a "grid point q before deformation", and the grid point corresponding to a representative point of the deformed image 202 will be called a "grid point p after deformation". In FIGS. 2A and 2B, grid points q before deformation and grid points p after deformation have the following relationship:

$$p0=f(q0),\ p1=f(q1),\ p2=f(q2),\ p3=f(q3),\ p4=f(q4),\ p5=f(q5)$$

where f( ) is a coordinate transformation operator in deformation.

In other words, when the coordinate transformation f( ) based on image deformation for conforming to the shape of a projection surface is performed on the coordinate values of the grid points q before deformation arranged in the pre-deformation image 201, the coordinate values of the grid points p after deformation are obtained. The coordinate values of the grid points p after deformation stored in the memory unit 106 may be calculated inside the projection apparatus 100 and stored in the memory unit 106, or may be calculated outside the projection apparatus 100 and stored in the memory unit 106.

The grid point determination unit 107 selects, from the plurality of grid points p after deformation stored in the memory unit 106, a set of grid points p after deformation to be used to calculate coordinate values before deformation. In the following description, a set of four grid points constituting a minimum quadrilateral not including a grid point after deformation inside it will be called a "block". In FIG. 2B, a block B0 is a set of grid points p0, p1, p2, and p3 after deformation, and a block B1 is a set of grid points p2, p3, p4, and p5 after deformation. Note that the shape of the block is not limited to a quadrilateral and may be a polygon. For example, the block may be a triangle having the grid points p0, p1, and p2 after deformation as vertices.

The selection of a set of grid points p after deformation is performed by inclusion determination of whether a quadrilateral (to be referred to as a "block quadrilateral" hereinafter) formed by four grid points p after deformation constituting a block includes a pixel of interest. Note that two triangles obtained by subdividing a quadrilateral, such as p0p1p2 and p1p2p3, may be set as inclusion determination targets.

Inclusion determination uses, for example, a crossing number algorithm. According to the crossing number algorithm, inclusion determination is performed based on the number of times by which a horizontal line starting from a pixel of interest crosses sides of a block quadrilateral. A block quadrilateral having an odd crossing number is determined to include a pixel of interest, and a block quadrilateral having an even crossing number is determined not to include a pixel of interest.

For example, a horizontal line starting from a pixel s0 of interest shown in FIG. 2B crosses a side of the block B0 quadrilateral only once, and sides of the block B1 quadrilateral twice. It is therefore determined that the pixel s0 of interest is included in the block B0 quadrilateral and is not included in the block B1 quadrilateral. Note that inclusion determination is not limited to the crossing number algorithm, and may use another algorithm such as a winding number algorithm.

Image deformation processing to be executed by the video deformation unit 103 according to the first embodiment will be explained with reference to the flowchart of FIG. 3. FIG. 3 shows image deformation processing of one pixel, and the processing shown in FIG. 3 is repeated for all the pixels of the output image 203.

The grid point determination unit 107 selects a block of interest (S11), and performs the inclusion determination of a pixel of interest (S12) so as to search for a block (to be referred to as an "inclusion block" hereinafter) including the pixel of interest. If the grid point determination unit 107 determines that the block of interest does not include the pixel of interest, it determines whether the inclusion determination has been performed for all blocks (S13). If there is an undetermined block, the grid point determination unit 107 returns the process to step S11.

For a pixel located outside the deformed image 202, like a pixel s2 shown in FIG. 2B, even if the inclusion determination is performed for all blocks, no inclusion block is detected. As for such a pixel of interest, the grid point determination unit 107 outputs, to the coordinate processing unit 108, information (to be referred to as "outside pixel information" hereinafter) representing that the pixel of interest exists not inside the deformed image 202 but outside the deformed image 202 (S14). On the other hand, if the grid point determination unit 107 detects an inclusion block, it outputs the coordinate values of the grid points p after deformation of the inclusion block to the coordinate processing unit 108 (S15).

The coordinate processing unit 108 calculates coordinate values before deformation from the coordinate values of the grid points p after deformation input from the grid point determination unit 107, and the coordinate values of the pixel of interest (S16). In FIG. 2B, when the pixel of interest is s0 and the inclusion block is B0, the coordinate values of a pixel t0 before deformation are calculated from the coordinate values of the pixel s0 of interest, the grid points p0, p1, p2, and p3 after deformation, and the grid points q0, q1, q2, and q3 before deformation that are paired with these grid points after deformation.

The calculation of coordinate values before deformation by the coordinate processing unit 108 will be explained with reference to FIGS. 4A and 4B. FIG. 4A is an enlarged view of the portion of the grid points q0, q1, q2, and q3 before deformation shown in FIG. 2A, and FIG. 4B is an enlarged view of the portion of the grid points p0, p1, p2, and p3 after deformation shown in FIG. 2B. The coordinate processing unit 108 obtains the relative position of the pixel s0 of interest in the quadrilateral p0p2p3p1, and fits the relative position to the pixel t0 before deformation in the quadrilateral q0q2q3q1, thereby obtaining the coordinate values of the pixel t0 before deformation.

First, the relative position is obtained using the triangle p0p2p3 or p0p3p1 including the pixel s0 of interest because the quadrilateral p0p2p3p1 is not a rectangle. The coordinate processing unit 108 performs the above-described inclusion determination for the triangles p0p2p3 and p0p3p1, determining a triangle (to be referred to as an "inclusion triangle" hereinafter) including the pixel s0 of interest (S161). Note that the inclusion triangle determination method is not limited. For example, it is apparent that the quadrilateral p0p2p3p1 includes the pixel s0 of interest, so a triangle (p0p2p3 or p0p3p1) including the pixel s0 of interest may be determined by comparing a diagonal p0p3 and the pixel s0 of interest. Note that when the grid point determination unit 107 targets a triangle as a block, the processing (S161) of determining a triangle can be omitted.

Next, the coordinate processing unit 108 obtains relative positions α and β of the pixel of interest in the inclusion triangle (S162). In FIG. 4B, an intersection point M of a straight line passing p0s0 and a line segment p2p3 is obtained, and the relative position α of the intersection point M on the line segment p2p3 is obtained by interpolation. Then, the relative position β of the pixel s0 of interest on the line segment p0M is obtained by interpolation. In this embodiment, the range of each of α and β is 0 (inclusive) to 1 (exclusive).

After that, the coordinate processing unit 108 applies the relative positions α and β to the relative position of the pixel t0 before deformation in the quadrilateral q0q2q3q1 of the grid points before deformation, obtaining the coordinate value of the pixel t0 before deformation (S163). First, a triangle corresponding to the inclusion triangle determined in step S161 is selected. For example, when the inclusion triangle is p0p2p3, the triangle q0q2q3 is selected. When the inclusion triangle is p0p3p1, the triangle q0q3q1 is selected. Then, the coordinate value of an intersection point N of a straight line passing q0t0 and a line segment q2q3 is obtained by interpolation of the line segment q2q3, and the coordinate values of the pixel t0 before deformation is obtained by interpolation of a line segment q0N.

When the coordinate processing unit 108 receives the outside pixel information from the grid point determination unit 107 for the pixel of interest, it outputs the outside pixel information to the pixel processing unit 105.

The pixel processing unit 105 calculates the pixel value of the pixel of interest of the deformed image 202 from the pixel value of a pixel in the pre-deformation image 201 that corresponds to the coordinate values before deformation calculated by the coordinate processing unit 108, and the pixel values of surrounding pixels of the pixel in the pre-deformation image 201 (S17). For example, in FIG. 2A, the pixel value of the pixel s0 of interest is calculated from the pixel value of the pixel t0 before deformation that corresponds to coordinates 205 before deformation, and the pixel values of surrounding pixels 206. In the calculation of the pixel value, a general bilinear method, bicubic method, or the like is used.

If the pixel processing unit 105 has received the outside pixel information through the coordinate processing unit 108 for the pixel of interest, it assigns a value indicating the outside of the deformed image 202 as the pixel value of the pixel of interest (S18). As the value indicating the outside of the deformed image 202, a value at which no light is projected when the output image 203 is projected, for example, (0, 0, 0) for the RGB values are used. The pixel processing unit 105 outputs the calculated or assigned pixel value of the pixel of interest to the output unit 102 (S19).

A pixel of interest for which it is determined that even less than one pixel falls outside the deformed image 202 is determined to exist outside the deformed image 202. The pixel processing unit 105 calculates the pixel value of the pixel of interest from the pixel value of a pixel corresponding to the coordinate values before deformation and the pixel values of the surrounding pixels. If a size of the pre-deformation image 201 and a size of the output image 203 are equal, there is no pixel of the pre-deformation image 201 that corresponds to the outside of the boundary of the deformed image 202 when calculating the pixel value of the boundary portion of the deformed image 202. As a result, no smooth image can be generated for the boundary portion of the deformed image 202. To generate a smooth image for the boundary portion of the deformed image 202, it is desirable to set the size of the pre-deformation image 201 to be slightly larger than that of the output image 203, or set the size of the output image 203 to be slightly smaller than that of the pre-deformation image 201.

By the above-described image deformation processing of the video deformation unit 103, the output image 203 including the deformed image 202 having undergone an arbitrary deformation in conformity with the shape of each of various projection surfaces is generated from the pre-deformation image 201. A video from which a viewer does not feel a distortion of the video can be projected.

In this manner, image deformation processing becomes possible, in which grid points used to calculate the coordinate values of a pixel of interest before deformation in the output image 203 are determined, and the pixel values of all the pixels of the output image 203 are calculated or assigned. This image deformation processing provides high-accuracy deformation calculation capable of coping with an arbitrary deformation. By setting the image size of the pre-deformation image 201 to be relatively large, a smooth image can be generated for the boundary portion of the deformed image 202.

Second Embodiment

A projection apparatus, an image processing apparatus, and an image processing method according to the second embodiment of the present invention will be described below. In the second embodiment, the same reference numerals as those in the first embodiment denote the same parts, and a detailed description thereof will not be repeated in some cases.

The first embodiment has explained an example of the arrangement in which blocks are unconditionally set as inclusion determination targets until an inclusion block is detected, in order to determine a set of grid points p after deformation to be used for coordinate transformation of a pixel of interest. According to this inclusion determination target block decision method, an inclusion block may be detected by a small number of times, or a final block may be detected as an inclusion block by performing the inclusion determination for all blocks. Further, when a pixel of interest exists outside the deformed image 202, the inclusion determination for all blocks is necessary. By the inclusion determination according to these procedures, the processing load of the grid point determination unit 107 is not small.

For example, when scanning is performed to move a pixel of interest forward in the main scanning direction, and if the pixel of interest reaches the right end of the output image 203, move the pixel of interest backward in the main scanning direction, the inclusion block of the pixel of interest is estimated to exist in or near the inclusion block of an immediately preceding pixel of interest. Hence, there is conceivable a method of determining a set of grid points p after deformation by only using the inclusion block of an immediately preceding pixel of interest and an adjacent block as inclusion determination targets. The second embodiment will explain an arrangement in which the processing load of a grid point determination unit 107 is reduced by decreasing the number of blocks to undergo the inclusion determination.

The arrangement of a projection apparatus 100 according to the second embodiment is shown in the block diagram of FIG. 5. As shown in FIG. 5, a coordinate transformation unit 104 according to the second embodiment comprises a generation unit 111 that generates grid points disposed outside an output image 203. The remaining arrangement is the same as the arrangement (FIG. 1) according to the first embodiment.

The generation unit 111 adds grid points (to be referred to as "extended grid points" hereinafter) to the outside of the output image 203. More specifically, the generation unit 111 stores the added extended grid points in a memory unit 106, in addition to existing grid points p after deformation stored in the memory unit 106. The extended grid points do not have paired grid points q before deformation, and are used to determine a set of grid points p after deformation without unconditionally setting blocks as inclusion determination targets by the grid point determination unit 107. That is, the grid point determination unit 107 can determine a set of grid points p after deformation by setting, as inclusion determination targets, a total of nine blocks, that is, a block including an immediately preceding pixel of interest and eight blocks adjacent to the inclusion block of the immediately preceding pixel of interest.

A state in which extended grid points are added is shown in FIG. 6. FIG. 6 shows some (16 points p11 to p44) grid points p after deformation shown in FIG. 2B. The generation unit 111 adds extended grid points to the grid points p after deformation. Points e00 to e40 and e01 to e04 each indicated by a sign □ in FIG. 6 are extended grid points disposed to the outside of the output image 203. When the upper left corner of the output image 203 is the origin $(x, y)=(0, 0)$, for example, the coordinate values of the extended grid point e01 are $(p11x, -1)$, and the coordinate values of the extended grid point e10 are $(-1, -p11y)$. p11x is the x-coordinate of the grid point p11, and p11y is the y-coordinate of the grid point p11. The coordinate values of the extended grid point e00 are $(-1, -1)$.

If the extended grid points $e_{xy}$ are added, as shown in FIG. 6, all pixels in the output image 203 are included in any block quadrilaterals. Note that the extended grid points $e_{xy}$ may be disposed not to outside the output image 203 but on the boundary of the output image 203. The coordinate values of the extended grid point e00 in this case are $(0, 0)$, similar to the origin.

Image deformation processing to be executed by a video deformation unit 103 according to the second embodiment will be explained with reference to the flowchart of FIG. 7. FIG. 7 shows image deformation processing of one pixel, and the processing shown in FIG. 7 is repeated for all the pixels of the output image 203.

The grid point determination unit 107 determines, as inclusion determination target blocks, blocks centered on a block (to be referred to as an "immediately preceding inclusion block" hereinafter) including an immediately preceding pixel of interest (S21). For example, when the pixel of interest is d3, the immediately preceding pixel of interest is d2, and the immediately preceding inclusion block is a quadrilateral p11p12p22p21, the following blocks serve as inclusion determination target blocks (a region 602 in FIG. 6 represents inclusion determination target blocks):

the quadrilateral of an immediately preceding inclusion block: p11p12p22p21 quadrilaterals adjacent to the immediately preceding inclusion block: e00e01p11e10, e01e02p12p11, e02e03p13p12, e10p11p21e20, p11p12p22p21, p12p13p23p22, e20p21p31e30, p21p22p32p31, and p22p23p33p32

When the pixel of interest is d1, the immediately preceding pixel of interest is d0, and the immediately preceding inclusion block is a quadrilateral e00e01p11e10, the following blocks serve as inclusion determination target blocks (a region 601 in FIG. 6 represents inclusion determination target blocks):
the quadrilateral of an immediately preceding inclusion block: e00e01p11e10 quadrilaterals adjacent to the immediately preceding inclusion block: e01e02p12p11, p11p12p22p21, and e10p11p21e20

Then, the grid point determination unit 107 selects a block of interest from the inclusion determination target blocks (S22), and performs the inclusion determination of a pixel of interest (S23) so as to search for an inclusion block. If the grid point determination unit 107 determines that the block of interest does not include the pixel of interest, it returns the process to step S22 to select the next block of interest. It is only necessary to perform the inclusion determination sequentially for a maximum of nine target blocks.

If the grid point determination unit 107 detects an inclusion block, it determines whether there is an extended grid point $e_{xy}$ as a vertex of the inclusion block (S24). If the inclusion block has not an extended grid point $e_{xy}$, the grid point determination unit 107 determines that the pixel of interest is included in a deformed image 202, and outputs the coordinate values of respective grid points p after deformation in the inclusion block to a coordinate processing unit 108 (S25). If the inclusion block has a extended grid point $e_{xy}$, the grid point determination unit 107 determines that the pixel of interest is located outside the deformed image 202, and outputs the outside pixel information to the coordinate processing unit 108 (S26). Subsequent processes (S16 to S19) are the same as those in the first embodiment, and the same reference numerals denote the same steps, and a description thereof will not be repeated.

In this way, inclusion determination target blocks are limited to a maximum of nine blocks by setting extended grid points $e_{xy}$, and it can be prevented that blocks are unconditionally set as inclusion determination targets until an inclusion block is detected. When a detected inclusion block has a extended grid point $e_{xy}$, it can be determined that the pixel of interest exists outside the deformed image 202. Accordingly, the number of blocks to undergo the inclusion determination can be decreased, the determination of whether the pixel of interest exists outside the deformed image 202 can be simplified, and the processing load of the grid point determination unit 107 can be reduced.

By imposing a constraint on grid points, only six blocks can be set as inclusion determination targets. More specifically, when a constraint representing that blocks do not cross each other on their four sides is imposed, the inclusion block is not retracted. The retraction is a transition in the left direction in which, when the inclusion block of a previous pixel of interest is a quadrilateral e01e02p12p11, the inclusion block of the next pixel of interest is a quadrilateral e00e01p11e10. Six blocks are 2×3 blocks obtained by excluding one column at the left end from 3×3 blocks. For example, when d3 in FIG. 6 is a pixel of interest, the six blocks serving as inclusion determination targets are the following quadrilaterals:
e01e02p12p11, e02e03p13p12, p11p12p22p21, p12p13p23p22, p21p22p32p31, and p22p23p33p32

Modification of Embodiments

The second embodiment has explained an example in which the inclusion determination target block is determined using an immediately preceding pixel of interest as a reference. However, it is only necessary to determine an inclusion determination target block by using, as a reference, a pixel having undergone inclusion determination that is adjacent to the top, bottom, left, or right of a pixel of interest or obliquely adjacent to it. For example, the grid point determination unit 107 holds information of the inclusion block of pixels of one line in the lateral direction, and sets, as the center of the inclusion determination target block, the inclusion block (to be referred to as a "previous inclusion block" hereinafter) of a pixel adjacent to a pixel of interest in the upper direction or upper oblique direction.

The second embodiment has explained an example in which the number of inclusion determination target blocks changes at the end portion of the output image 203. However, there is conceivable a method in which the number of inclusion determination target blocks does not change. FIG. 8 shows another addition example of extended grid points $e_{xy}$. Referring to FIG. 8, extended grid points eaa to e4a and ea0 to ea4 are added outside the extended grid points e00 to e40 and e01 to e04 shown in FIG. 6. That is, the extended grid points $e_{xy}$ are added double outside the output image 203. Note that the coordinate value of the extended grid point ea1 is (p11x, −2), and that of the extended grid point e1a is (−2, p11y).

In FIG. 8, for example, when the pixel of interest is d1, and the immediately preceding pixel of interest is d0, there are nine inclusion determination target blocks, as represented by a region 701, and 3×3 blocks can be set as inclusion determination target blocks for all pixels of interest in the output image 203.

The first embodiment has explained an example in which inclusion determination is performed based on grid points after deformation prepared in advance. The second embodiment has explained an example in which the extended grid points $e_{xy}$ are introduced and inclusion determination target blocks are determined using a pixel having undergone inclusion determination as a reference. However, the extended grid points $e_{xy}$ can also be introduced into the arrangement according to the first embodiment. In this case, if a detected inclusion block includes the extended grid points $e_{xy}$, it can be quickly determined that the pixel of interest is located outside the deformed image 202. In other words, when the pixel of interest is located outside the deformed image 202, the possibility at which inclusion determination need not be performed for all blocks increases.

The determination of inclusion determination target blocks using a pixel having undergone inclusion determination as a reference can also be introduced into the arrangement according to the first embodiment. In this case, the detection of an inclusion block can be completed in a short time. When the pixel of interest is located outside the deformed image 202, inclusion determination for all blocks is necessary.

An example in which the video deformation unit 103 is incorporated in the projection apparatus 100 has been explained above. However, the video deformation unit 103 can also be implemented as an image processing apparatus using a computer apparatus. More specifically, a program that implements the function of the video deformation unit 103, and data of grid points after deformation are supplied to the computer apparatus through a recording medium or a network. Then, the computer apparatus inputs the pre-deformation image 201, and supplies the output image 203 including the deformed image 202 to the projection apparatus 100.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)®), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-226408 filed Nov. 6, 2014 which is hereby incorporated by reference herein in its entirety.

The invention claimed is:

1. An image processing apparatus for deforming a first image into a second image and generating a third image which contains the second image, the image processing apparatus comprising:
a memory unit configured to store coordinate values indicating a position of each of a plurality of grid points after deformation disposed in the second image; and
a determination unit configured to determine whether a pixel of interest in the third image is located in the second image or the pixel of interest in the third image is located outside of the second image, based on the coordinate values stored in the memory unit,
wherein the determination unit further decides a set of grid points after deformation corresponding to the pixel of interest from the plurality of grid points after deformation.

2. The image processing apparatus according to claim 1, further comprising:
a coordinate processing unit configured to calculate coordinate values indicating a pixel position in the first image corresponding to the pixel of interest, based on the set of grid points after deformation; and
a pixel processing unit configured to calculate a pixel value of the pixel of interest from the first image, based on the coordinate values indicating the pixel position in the first image.

3. The image processing apparatus according to claim 2, wherein in a case when it is determined that the pixel of interest locates outside the second image, the determination unit outputs outside pixel information, and
wherein in a case when the determination unit outputs the outside pixel information, the pixel processing unit assigns a value representing the outside of the second image as a pixel value of the pixel of interest.

4. The image processing apparatus according to claim 2, wherein the pixel processing unit provides the pixel value of the pixel of interest as the third image to a video projection unit.

5. The image processing apparatus according to claim 1, wherein the determination unit is configured to perform:
selecting a polygon which has at least three grid points contained in the plurality of grid points after deformation as vertices and has no grid point after deformation inside that;
executing inclusion determination to determine whether the selected polygon includes the pixel of interest or not; and
deciding, in a case when it is determined that the selected polygon includes the pixel of interest, the grid points after deformation corresponding to the vertices of the selected polygon as the set of grid points after deformation.

6. The image processing apparatus according to claim 5, wherein in a case when it is determined that all polygons defined by the grid points after deformation do not include the pixel of interest, the determination unit determines that the pixel of interest locates outside the second image.

7. The image processing apparatus according to claim 5, wherein the determination unit selects the polygon to be a subject of the inclusion determination of the pixel of interest based on an adjacent pixel adjacent to the pixel of interest, and the inclusion determination of the adjacent pixel has been completed.

8. The image processing apparatus according to claim 7, wherein the determination unit selects a first polygon including the adjacent pixel and a second polygon adjacent to the first polygon as the subject of the inclusion determination.

9. The image processing apparatus according to claim 1, further comprising a generation unit configured to generate a plurality of extended grid points disposed on a boundary or outside of the third image,
wherein the determination unit is configured to perform:
(a) selecting a polygon which has at least three grid points contained in the plurality of grid points after deformation and the plurality of extended grid points, and has no grid point after deformation or no extended grid point inside that,
(b) executing inclusion determination to determine whether the selected polygon includes the pixel of interest or not, and
(c) deciding, in a case when it is determined that the selected polygon which has no extended grid point as a vertex includes the pixel of interest, the grid points after deformation corresponding to the vertices of the selected polygon as the set of grid points after deformation.

10. The image processing apparatus according to claim 9, wherein in a case when it is determined that the selected polygon which has an extended grid point as a vertex includes the pixel of interest, the determination unit determines that the pixel of interest locates outside the second image.

11. A video projection apparatus comprising the image processing apparatus according to claim 1.

12. An image processing method of deforming a first image into a second image and generating a third image which contains the second image, the image processing method comprising:
   storing coordinate values indicating a position of each of a plurality of grid points after deformation disposed in the second image;
   determining whether a pixel of interest in the third image is located in the second image or the pixel of the interest in the third image is located outside of the second image, based on the stored coordinate values; and
   deciding a set of grid points after deformation corresponding to the pixel of interest from the plurality of grid points after deformation.

13. A non-transitory computer-readable storage medium storing a computer program for causing a computer to execute an image processing method of deforming a first image into a second image and generating a third image which contains the second image, the image processing method comprising:
   storing coordinate values indicating a position of each of a plurality of grid points after deformation disposed in the second image;
   determining whether a pixel of interest in the third image is located in the second image or the pixel of the interest in the third image is located outside of the second image, based on the stored coordinate values; and
   deciding a set of grid points after deformation corresponding to the pixel of interest from the plurality of grid points after deformation.

\* \* \* \* \*